US00PP16468P3

(12) United States Plant Patent

Miyazaki et al.

(10) Patent No.: US PP16,468 P3

(45) Date of Patent: Apr. 18, 2006

(54) *PETUNIA* PLANT NAMED 'SUNROVEIN'

(50) Latin Name: *Petunia hybrida*
Varietal Denomination: Sunrovein

(75) Inventors: Kiyoshi Miyazaki, Hikone (JP); Kazunari Iwaki, Omihachiman (JP); Takuro Ishihara, Higashikurume (JP); Kenichi Suzuki, Ibaraki (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 23 days.

(21) Appl. No.: 10/789,408

(22) Filed: Feb. 26, 2004

(65) Prior Publication Data

US 2005/0193456 P1 Sep. 1, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP9,322 | P | 10/1995 | Tachibana et al. |
| PP10,279 | P | 3/1998 | Murakami |
| PP10,355 | P | 4/1998 | Murakami |

FOREIGN PATENT DOCUMENTS

| | | |
|---|---|---|
| JP | PBR REG. 7229 | 6/1999 |
| JP | PBR REG. 7232 | 6/1999 |

OTHER PUBLICATIONS

Explanation of Publication of Japanese PBR Registration and family documents thereof.
Explanation for IDS Documents.
Suntory Flowers Ltd., "Flowers & Green, the newest catalog 2004" Published 2003.
Jackson & Perkins Wholesale, Inc., USA, "The 2004 Suntory Collection" Published 2003.
Pineae Greenhouses, Inc., USA, "featuring the 2004 Suntory Collection" Published 2003.
Moerheim New Plant bv., USA, "Suntory Collection 2004" Published 2003.
Ramm Botanicals Pty Ltd., AU., "Colour Wave Collection 2003–4" Published 2002.

*Primary Examiner*—Kent Bell
(74) *Attorney, Agent, or Firm*—Christie, Parker and Hale, LLP

(57) ABSTRACT

Disclosed herein is a new and distinct variety of *Petunia* plant having a decumbent growth habit. The *Petunia* plant has abundant branching, and great profusion of blooms, the whole plant remaining in bloom for a considerable period of time. The flowers are single and medium size, the petals having vivid purplish red color with deep purplish red vein. The bottom color of the corolla throat is moderate purplish red and the outside of the corolla tube is light purplish pink. The plant exhibits high resistance to rain, heat, cold and diseases.

2 Drawing Sheets

Botanical classification: *Petunia hybrida.*
Varietal denomination: 'Sunrovein'.

BACKGROUND OF THE VARIETY

The *Petunia* is a very popular plant that is used for flower bedding and potting in the summer season. There are only a few *Petunia* varieties which do not have an upright growth habit and which have a high resistance to rain, heat, and diseases. The *Petunia* plant varieties for which we previously filed patent applications, i.e., the 'Revolution' series ('Revolution Purple Pink' (U.S. Plant Pat. No. 6,915), 'Revolution Brilliant pink' (U.S. Plant Pat. No. 6,914), 'Revolution Brilliant pink-mini' (U.S. Plant Pat. No. 6,899), and 'Revolution Blue vein' (U.S. Plant Pat. No. 9,322)) are decumbent type plants having long stems, a lower plant height, abundant branching, and a high resistance to heat, rain and diseases. However, there are only a few *Petunia* varieties having a great profusion of flowers, vivid colored flower petals and a high resistance to rain, heat, cold and diseases. Accordingly, this invention was aimed at obtaining a new variety which had many flowers having vivid purplish red colored petals with deep purplish red vein, many branching and decumbent growth habit together with the above features.

The present new distinct cultivar of *Petunia* was created by heavy ion beam irradiation of the *Petunia* hybrid variety called 'Revolution briliiant pink'. 'Revolution brilliant pink' (U.S. Plant Pat. No. 6,914) is our *Petunia* hybrid variety and is grown in Shiga, Japan.

In November 1999, 5 Gy of ionic neon (135 MeV) were irradiated on 128 pieces of in-vitro meristems of 'Revolution brilliant pink' using the Ring Cyclotron at the Institute of Physical and Chemical Research in Japan. All shoots developed from irradiated meristems were planted in soil in a greenhouse. In April 2000, we selected a plant having vivid purplish red petals with a deep purplish red pattern. That plant was propagated by cutting, grown in pots and used in a trial in April 2001 in Yokaichi, Shiga, Japan. By October 2001, the botanical characteristics of that plant were examined. As a result, it was concluded that this new *Petunia* plant is distinguishable from any other variety, whose existence is known to us, and is uniform and stable in its characteristics. This new variety of *Petunia* plant was named 'Sunrovein'.

The new variety of *Petunia* plant 'Sunrovein' was asexually reproduced by cutting at Yokaichi-shi, Shiga-ken, Japan, and the homogeneity and stability thereof were confirmed. The instant plant retains its distinctive characteristics and reproduces true to type in successive generations.

In the following description, the color-coding is in accordance with the Horticultural Colour Chart of The Royal Horticultural Society, London, England (R.H.S.).

The parent used to obtain this new variety 'Sunrovein' was 'Revolution brilliant pink' having very spreading habit and many branches. It has medium single flowers having vivid purplish red (near R.H.S. 74A) petals. The bottom color of the corolla throat is dark purple (near R.H.S. 83A) and outside color of the corolla tube is deep purplish pink (near R.H.S. 70C).

The main botanical characteristics of the 'Revolution brilliant pink' are as follows:

Plant:
- *Growth habit.*—Decumbent.
- *Plant height.*—Approximately 15 cm.
- *Spreading area of plant.*—Very large; approximately 100 cm.
- *Blooming period.*—Mid April to late October in the southern Kanto area, Japan.

Stem:
- *Thickness.*—Main stem, approximately 3.0 mm.
- *Pubescence.*—Normal.
- *Branching.*—Many.
- *Length of internode.*—Approximately 3.0 cm.
- *Color.*—Moderate olive green (near R.H.S. 146A).

Leaf:
- *Whole shape.*—Lanceolate. The apex shape is acute, and the base shape is attenuate.
- *Length.*—Approximately 6.0 cm.
- *Width.*—Approximately 3.5 cm.
- *Color.*—Upper-side color is moderate olive green (near R.H.S. 146A). Bottom-side color is moderate yellow green (near R.H.S. 147B).
- *Pubescence.*—Sparse.

Flower:
- *Facing direction.*—Slanted upward.
- *Type.*—Single.
- *Shape of corolla tube.*—Thick.
- *Shape of petal tip.*—Acute.
- *Lobation.*—Medium.
- *Waviness of petal.*—Weak.
- *Diameter.*—Approximately 7.5 cm.
- *Color.*—Petal; vivid purplish red (near R.H.S. 74A). Bottom color of the corolla throat; dark purple (near R.H.S. 83A). Outside color of the corolla tube; deep purplish pink (near R.H.S. 70C).
- *Reproductive organs.*—1 normal pistil and 5 normal stamens. Color of pistil is grayish olive green (near R.H.S. 137A). Color of stamen is light purple (near R.H.S. 87D).
- *Peduncle.*—Approximately 1.0 mm in thickness, and approximately 2.0 cm in length.

Physiological and ecological characteristics; Moderate resistance to cold and pests. Strong resistance to rain, heat and diseases.

The main botanical characteristics of similar variety 'Sunrove' (U.S. Plant Pat. No. 14,125) used for comparison are as follows:

Plant:
- *Growth habit.*—Decumbent.
- *Plant height.*—Approximately 10.5 cm.
- *Spreading area of plant.*—Approximately 75 cm.
- *Blooming period.*—Early April to late October in the southern Kanto area, Japan.

Stem:
- *Thickness.*—Main stem approximately 1.8 mm.
- *Pubescence.*—Dense.
- *Branching.*—Many.
- *Length of internode.*—Approximately 0.9 cm.
- *Color.*—Strong yellow green (near R.H.S. 144B).

Leaf:
- *Whole shape.*—Elliptic. The apex shape is acute, and the base shape is attenuate.
- *Length.*—Approximately 8.0 cm.
- *Width.*—Approximately 4.4 cm.
- *Color.*—Upper-side color is moderate olive green (near R.H.S. 146A). Bottom-side color is moderate yellow green (near R.H.S. 147B).
- *Pubescence.*—Normal.

Flower:
- *Facing direction.*—Slanted upward.
- *Type.*—Single.
- *Shape of corolla tube.*—Medium.
- *Shape of petal tip.*—Rounded.
- *Lobation.*—Shallow.
- *Waviness of petal.*—Weak.
- *Diameter.*—Approximately 5.5 cm.
- *Color.*—Petal; light purplish pink (near R.H.S. 73C) with vivid reddish purple (near R.H.S. 74A) vein. Bottom color of the corolla throat; brilliant purple (near R.H.S. 81C). Outside color of the corolla tube; very pale violet (near R.H.S. 92D).
- *Reproductive organs.*—1 normal pistil and 5 normal stamens. Color of pistil is strong yellow green (near R.H.S. 144B). Color of stamen is light purple (near R.H.S. 85A).
- *Peduncle.*—Approximately 0.7 mm in thickness, and approximately 1.7 cm in length.

Physiological and ecological characteristics; Moderate resistance to cold and pests. Strong resistance to rain, heat and diseases.

The main botanical characteristics of similar variety 'Revolution hotpink marrose' (U.S. Plant Pat. No. 10,904) used for comparison are as follows:

Plant:
- *Growth habit.*—Decumbent.
- *Plant height.*—Approximately 16 cm.
- *Spreading area of plant.*—Large.
- *Blooming period.*—Early April to late October in the southern Kanto area, Japan.

Stem:
- *Thickness.*—Main stem, approximately 3.0 mm.
- *Pubescence.*—Normal.
- *Branching.*—Many.
- *Length of internode.*—Approximately 3.0 cm.
- *Color.*—Moderate olive green (near R.H.S. 146A).

Leaf:
- *Whole shape.*—Lanceolate. The apex shape is acute, and the base shape is attenuate.
- *Length.*—Approximately 5.5 cm.
- *Width.*—Approximately 4.0 cm.
- *Color.*—Upper-side color is moderate olive green (near R.H.S. 146A). Bottom-side color is moderate yellow green (near R.H.S. 147B).
- *Pubescence.*—Normal.

Flower:
- *Facing direction.*—Slanted upward.
- *Type.*—Single.

*Shape of corolla tube.*—Thick.
*Shape of petal tip.*—Acute.
*Lobation.*—Medium.
*Waviness of petal.*—Weak.
*Diameter.*—Approximately 7.5 cm.
*Color.*—Petal; deep purplish pink (near R.H.S. 61D) with dark reddish purple (near R.H.S. N79B) vein. Bottom color of the corolla throat; deep purple (near R.H.S. 83A). Outside color of the corolla tube; deep purplish pink (near R.H.S. 61D).
*Reproductive organs.*—1 normal pistil and 5 normal stamens. Color of pistil is grayish olive green (near R.H.S. 137A). Color of stamen is light purple (near R.H.S. 87D).
*Peduncle.*—Approximately 1.0 mm in thickness, and approximately 2.0 cm in length.

Physiological and ecological characteristics;—Moderate resistance to pests. Strong resistance to cold, rain, heat and diseases.

SUMMARY OF THE VARIETY

The new variety of the *Petunia* plant has a decumbent growth habit, abundant branching and great profusion blooms with the whole plant remaining in bloom for a considerable period of time. The flowers are single and medium size. The petal color is vivid purplish red with deep purplish red vein. The plant has a high resistance to rain, cold, heat and diseases.

BRIEF DESCRIPTION OF THE PHOTOGRAPHS

The plants were reproduced by cutting and were photographed in September 2002 while growing outdoors in 24 cm pots at an age of approximately 6 months at Yokaichi-shi, Shiga-ken, Japan.

DESCRIPTION OF THE NEW VARIETY

Figure 1:
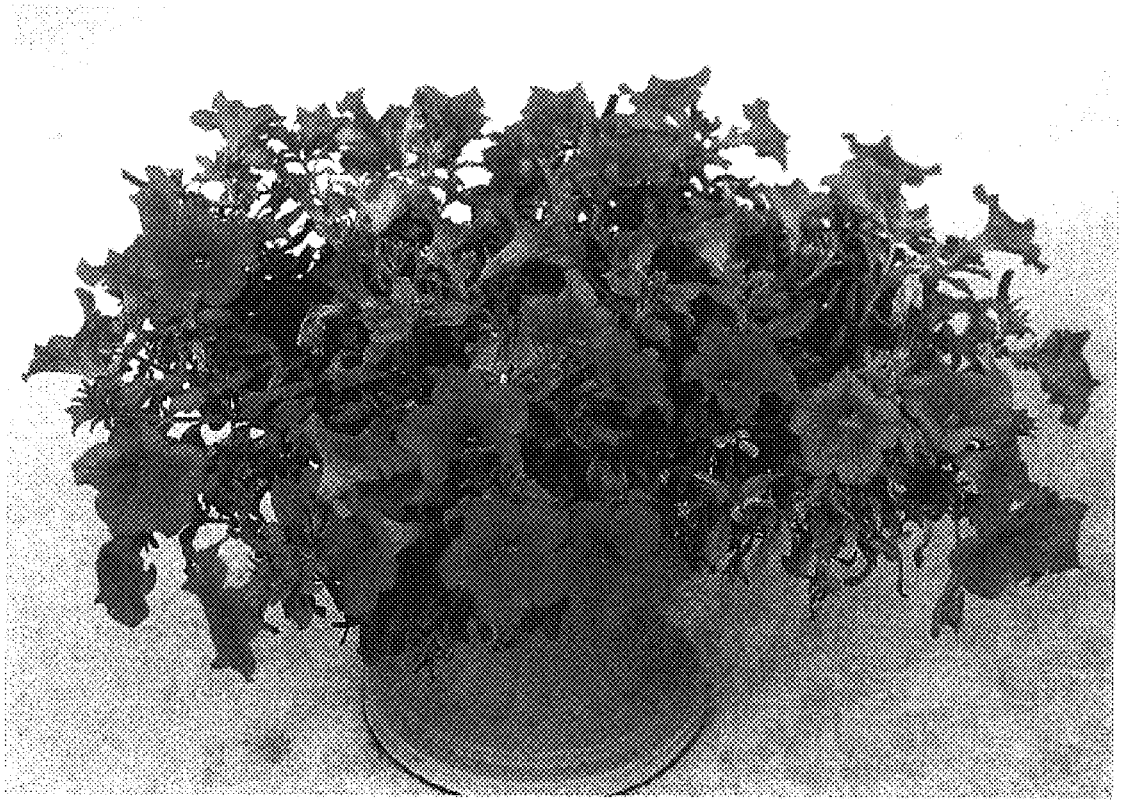
FIG. 1 is a photograph of flowers and leaves of the new variety of *Petunia* plant 'Sunrovein'.
Figure 2:
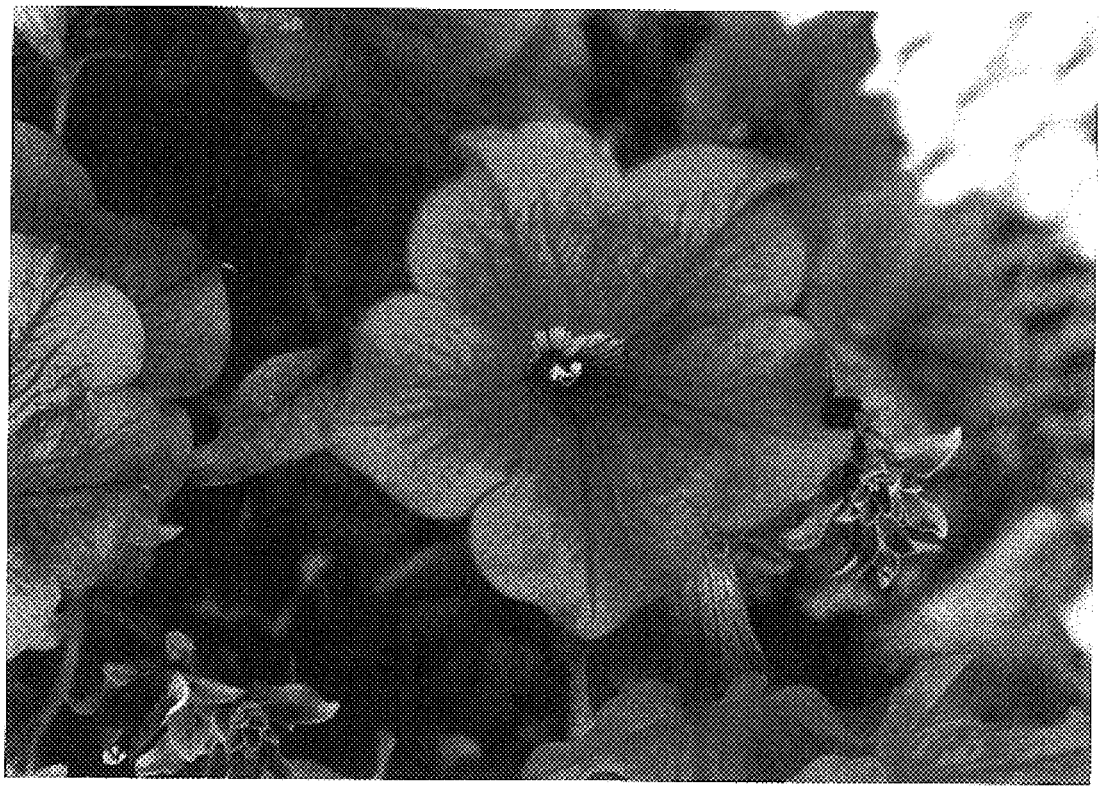
FIG. 2 is a close-up photograph of flowers of the new variety of *Petunia* plant 'Sunrovein'.

The botanical characteristics of the new and distinct variety of *Petunia* plant named 'Sunrovein', observed during September 2002 at Yokaichi-shi, Shiga-ken, Japan at an age of approximately 6 months, are as follows:

Plant:
*Growth habit.*—Decumbent.
*Plant height.*—Approximately 25 cm.
*Spreading area of plant.*—Approximately 80 cm.
*Blooming period.*—Mid April to late October in the southern Kanto area, Japan.

Stem:
*Length.*—Approximately 14.7 cm.
*Thickness.*—Main stem approximately 2.2 mm.
*Pubescence.*—Normal.
*Branching.*—Approximately 21.
*Length of internode.*—Approximately 2.0 cm.
*Color.*—Modetate olive green (near R.H.S. 146A).

Leaf:
*Whole shape.*—Elliptic. The apex shape is acute, and the base shape is attenuate.
*Margin.*—Entire.
*Length.*—Approximately 4.8 cm.
*Width.*—Approximately 3.2 cm.
*Color.*—Upper-side color is moderate olive green (near R.H.S. 146A). Bottom-side color is moderate yellow green (near R.H.S. 147B).
*Pubescence.*—Moderate.

Flower:
*Facing direction.*—Horizontal.
*Type.*—Single.
*Shape of corolla tube.*—Obconical.
*Shape of petal tip.*—Obtuse.
*Lobation.*—Medium.
*Waving of petal.*—Medium.
*Diameter.*—Approximately 7.0 cm.
*Flower depth.*—Approximately 4.9 cm.
*Throat diameter (distal end).*—Approximately 16.6 mm.
*Corolla tube diameter (proximal end).*—Approximately 8 mm.
*Corolla tube length.*—Approximately 2.7 cm.
*Number of petals.*—Approximately 5.
*Shape of petal.*—Very broadly obovate.
*Petal length.*—Approximately 3.1 cm.
*Petal width.*—Approximately 3.2 cm.
*Apex shape.*—Mucronate.
*Margin.*—Entire, undulated.
*Color.*—Petal; Upper — vivid purplish red (near R.H.S. 71B) with deep purplish red (near R.H.S. 71A) vein, lower — near R.H.S. 70C. Inside color of the corolla throat; moderate purplish red (R.H.S. N77B). Outside color of the corolla tube; light purplish pink (near R.H.S. 62D).

Sepal:
*Number.*—Approximately 5.
*Shape.*—Oblong.
*Apex shape.*—Rounded.
*Margin.*—Entire.
*Length.*—Approximately 2.0 cm.
*Width.*—Approximately 1.0 cm.
*Color.*—Upper surface — Near R.H.S. 144A; Lower surface — Near R.H.S. 144B.
*Reproductive organs.*—1 pistil and 5 stamens. Color of pistil is grayish olive green (near R.H.S. 137A). Color of stamen is light purple (near R.H.S. 87D).
*Peduncle.*—Approximately 1.7 mm in thickness, and approximately 2.0 cm in length. Color — Near R.H.S. 144B.
*Lastingness of the bloom.*—Approximately 5 days.
*Fragrance.*—Absent.

Physiological and ecological characteristics;—Moderate resistance to pests. Strong resistance to cold, rain, heat and diseases.

This new variety of *Petunia* plant is most suitable for flower bedding, potting and large planters. Pinching of old blossoms will enhance the formation of new blossoms.

A new and distinct variety of *Petunia hybrida* plant named 'Sunrovein', substantially as herein illustrated and described.

I claim:

1. A new and distinct variety of *Petunia hybrida* plant named 'Sunrovein', substantially as herein illustrated and described.

* * * * *